United States Patent [19]
Hobbins

[11] Patent Number: 5,922,947
[45] Date of Patent: Jul. 13, 1999

[54] SILICA CARBIDE TRANSDUCER FOR ULTRASONIC NEBULIZERS EMPLOYED IN ATOMIC SPECTROSCOPY

[75] Inventor: William B. Hobbins, Englewood, Colo.

[73] Assignee: Precision Instrumentation, Ltd., Englewood, Colo.

[21] Appl. No.: 08/815,720

[22] Filed: Mar. 12, 1997

[51] Int. Cl.⁶ ........................................................ G01N 9/00
[52] U.S. Cl. ............................................................ 73/64.56
[58] Field of Search ................................ 73/863, 863.11, 73/864.81, 61.59, 64.56, 864.56; 250/288; 356/36, 326

[56] References Cited

U.S. PATENT DOCUMENTS 4,926,085  5/1990  Sawayama et al. .
5,411,208  5/1995  Burgener ...................................... 239/8

*Primary Examiner*—Robert Raevis
*Attorney, Agent, or Firm*—William E. Hein

[57] ABSTRACT

An ultrasonic nebulizer employs a transducer whose face or diaphragm is constructed of silica carbide, which is impervious to sample solutions containing hydrofluoric acid, to thereby permit analysis of those solutions in a system in which the ultrasonic nebulizer is connected to an inductively coupled plasma spectrometer or to an inductively coupled plasma mass spectrometer.

3 Claims, 1 Drawing Sheet

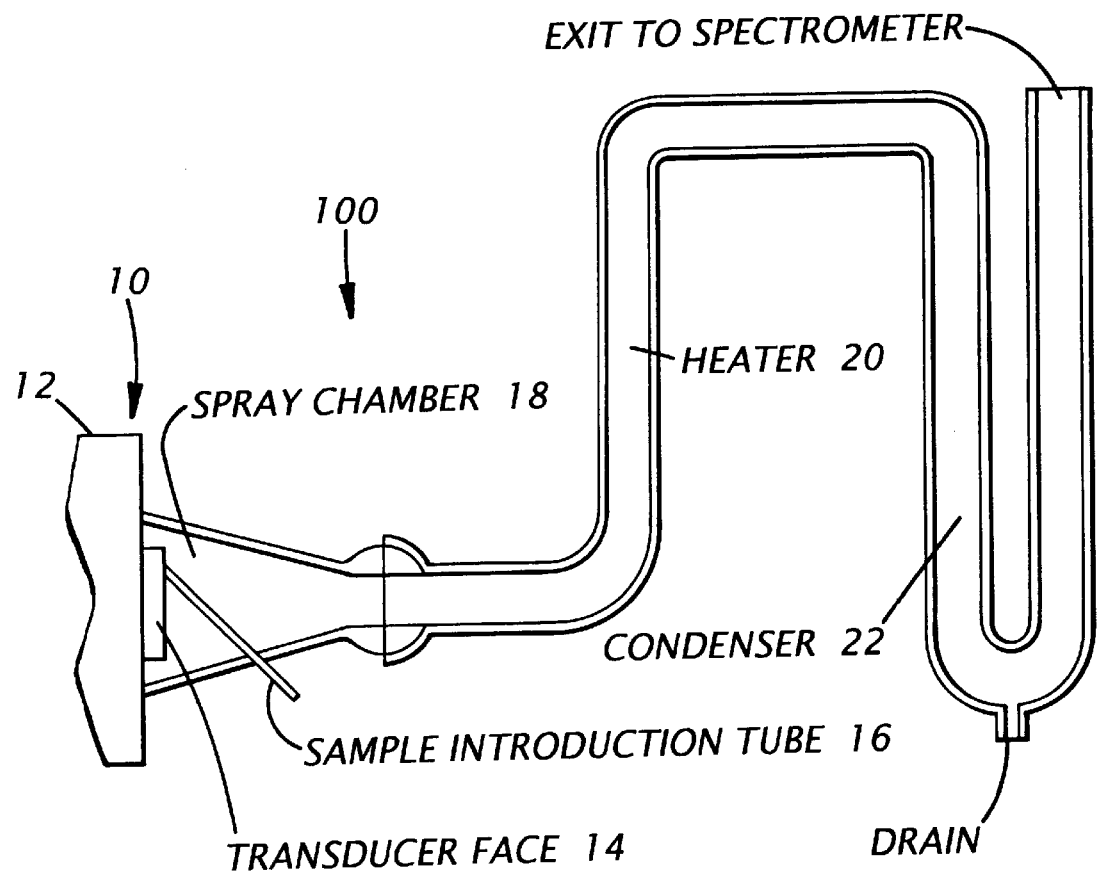
FIG. 1
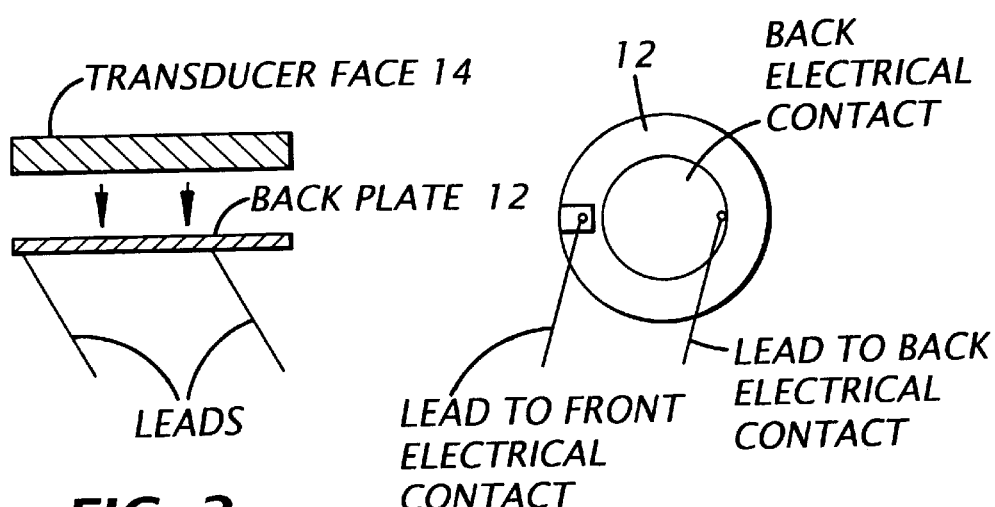
FIG. 2
FIG. 3

SILICA CARBIDE TRANSDUCER FOR ULTRASONIC NEBULIZERS EMPLOYED IN ATOMIC SPECTROSCOPY

BACKGROUND AND SUMMARY OF THE INVENTION

This invention relates generally to ultrasonic nebulizers and, more particularly, to an ultrasonic nebulizer that may be used for the analysis of samples containing hydrofluoric acid.

Inductively coupled plasma (ICP) spectrometers and ICP mass spectrometers (ICP-MS) have been used for trace level elemental analysis world wide. Samples are most commonly introduced to these prior art instruments in liquid form by means of a nebulizer, which creates an aerosol that is swept into the ICP spectrometer plasma by flowing argon gas. Traditionally, these samples have been introduced using a pneumatic nebulizer, but over the past ten years ultrasonic nebulizers have become commercially available.

Samples are presented to the ICP spectrometer of ICP-MS in a variety of liquids, depending on a particular liquid's suitability as a solvent for the sample. For example, mineral samples are usually dissolved in a solution of water and nitric acid. For analysis of wear metal in lubricating oils, an organic solvent is used. Silicate samples are often presented in a solution of water and hydrofluoric acid.

Pneumatic nebulizers have been constructed of various materials, most commonly quartz or borosilicate glass. These nebulizers can produce an aerosol from most liquids, with the exception of samples containing hydrofluoric acid (HF), which effectively dissolves glass. There are, however, several pneumatic nebulizers which have been constructed of HF-resistant materials, such as that described in U.S. Pat. No. 5,411,208 to Burgener and others constructed of Teflon™, PEEK™, and Kynar™, all of which are commercially available.

Pneumatic nebulizers are relatively inefficient producers of aerosols, with usually 98% or more of the sample eliminated from the sample stream and going to waste. Ultrasonic nebulizers have been used to improve the sensitivity of the ICP spectrometer and ICP-MS with their inherent increased nebulization efficiency as compared to pneumatic nebulizers. Due to a combination of more efficient aerosol formation and smaller aerosol droplet size, ultrasonic nebulizers can improve sensitivity of the spectrometer by a factor of 10–50. However, these nebulizers cannot be used in the analysis of samples containing HF because the quartz transducer face of the nebulizer is glass, which will be dissolved by the HF.

Ultrasonic nebulizers are well understood devices for the introduction of liquid samples into ICP spectrometers. They have been utilized for the analysis of samples dissolved in both aqueous and organic solvents and a variety of acid-containing solutions, with the exclusion of samples containing HF. The analysis of samples containing HF has heretofore been impossible because one of the critical components of the ultrasonic nebulizer, the transducer face or diaphragm, has been fabricated of quartz glass, a material that is readily attacked and destroyed by HF.

The transducer is a critical component of the ultrasonic nebulizer. It consists of a vibrating metal plate to which is fixed a glass face or diaphragm. The sample liquid passes over this diaphragm and is converted to an aerosol. Since the transducer face is in contact with the sample, it is essential that the material of which it is constructed be impervious to the sample being analyzed in order to prevent contamination of the sample. If the sample dissolves the diaphragm, it also damages it sufficiently to prevent formation of an aerosol. For these reasons, it has not been possible to use conventional ultrasonic nebulizers in conjunction with samples containing HF. Traditional HF-resistant materials such as Teflon™ are not suitable as diaphragms, since they lack the proper density needed to create an aerosol. Attempts to coat conventional glass diaphragms with Teflon™ or some other HF-resistant material have resulted in poor aerosol formation.

It is therefore the principal object of the present invention to provide a transducer that will effectively produce an aerosol from solutions containing hydrofluoric acid, for use in an ultrasonic nebulizer connected to an inductively coupled plasma spectrometer or ICP-MS.

It is a further object of the present invention to provide a transducer having a diaphragm that is impervious to HF solutions, but that wets properly and forms an adequate aerosol.

These and other incidental objects are accomplished in accordance with the illustrated preferred embodiment of the present invention by providing a silica carbide wafer having a specific thickness as the face or diaphragm of the transducer. This material provides the proper density, wettability, and resistance to HF required to enable its use in the analysis of HF solutions.

BRIEF DESCRIPTION OF THE DRAWINGS

FIG. 1 is pictorial diagram illustrating the principal components of an ultrasonic nebulizer that may be coupled to a spectrometer to facilitate analysis of liquid samples.

FIG. 2 is a detailed pictorial diagram illustrating the transducer portion of the ultrasonic nebulizer of FIG. 1.

FIG. 3 is a detailed pictorial diagram illustrating the back plate of the transducer of FIG. 2.

DETAILED DESCRIPTION OF THE PREFERRED EMBODIMENT

Referring now to FIGS. 1–3 there is shown an ultrasonic nebulizer 100 having a transducer assembly 10. Transducer assembly 10 includes a back plate 12 having electrical leads attached thereto for receiving a conventional electrical drive signal, a transducer face 14, a sample introduction tube 16, and a spray chamber 18. A liquid sample passes through the sample introduction tube 16 and onto the transducer face 14, whose ultrasonic vibrations produced by the drive signal applied to the back plate 12 produces an aerosol that is swept from the spray chamber to a heater 20, which vaporizes the sample at 140 degrees C., or some other temperature that is appropriate for the sample being analyzed. The vaporized sample then passes into a condenser 22, where it is cooled to 5 degrees C. By heating and then cooling the sample, solvent to the ICP spectrometer plasma is reduced, and sensitivity of the overall nebulizer-ICP spectrometer system is enhanced.

In accordance with the present invention, the transducer face 14 of the transducer assembly 10 of the ultrasonic nebulizer 100 is constructed of silica carbide, formed as a wafer of specific thickness. Determination of the correct thickness of the silica carbide wafer is based on the transmission of sound through the material and the frequency of the vibration desired. The thickness of the silica carbide wafer acting as the transducer face or diaphragm 14 is computed by dividing the speed of sound through the silica carbide material by the vibrational frequency and by then dividing the result by two or four. The diameter of the transducer face 14 is not critical, so long as it fits into the nebulizer being used. At stated above, by constructing transducer face 14 of silica carbide, which is impervious to hydrofluoric acid, samples containing HF, which could not previously be analyzed, may now be readily analyzed.

I claim:

1. An ultrasonic nebulizer having a transducer back plate for receiving an electrical drive signal, a transducer face bonded to the transducer back plate, a spray chamber surrounding the transducer face, and a sample introduction tube for introducing a liquid sample onto the transducer face, wherein the improvement comprises fabricating the transducer face of silica carbide.

2. An ultrasonic nebulizer as in claim 1, wherein the silica carbide transducer face has a thickness computed by dividing the speed of sound through the silica carbide by a desired vibrational frequency and by then dividing the result by two.

3. An ultrasonic nebulizer as in claim 1, wherein the silica carbide transducer face has a thickness computed by dividing the speed of sound through the silica carbide by a desired vibrational frequency and by then dividing the result by four.

* * * * *